United States Patent
Jiang et al.

(10) Patent No.: US 10,096,447 B1
(45) Date of Patent: Oct. 9, 2018

(54) ELECTRON BEAM APPARATUS WITH HIGH RESOLUTIONS

(71) Applicant: KLA-Tencor Corporation, Milpitas, CA (US)

(72) Inventors: Xinrong Jiang, Palo Alto, CA (US); Christopher Sears, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/666,666

(22) Filed: Aug. 2, 2017

(51) Int. Cl.
| | |
|---|---|
| H01J 37/145 | (2006.01) |
| H01J 37/244 | (2006.01) |
| H01J 37/28 | (2006.01) |
| H01J 37/073 | (2006.01) |
| H01J 37/075 | (2006.01) |
| G01N 23/2251 | (2018.01) |

(52) U.S. Cl.
CPC ........ H01J 37/145 (2013.01); G01N 23/2251 (2013.01); H01J 37/073 (2013.01); H01J 37/075 (2013.01); G01N 2223/418 (2013.01); G01N 2223/6116 (2013.01)

(58) Field of Classification Search
USPC .... 250/306, 307, 310, 397, 398, 396 R, 526
See application file for complete search history.

(56) References Cited

U.S. PATENT DOCUMENTS

| | | | |
|---|---|---|---|
| 5,493,116 A * | 2/1996 | Toro-Lira | H01J 37/28 250/310 |
| 6,664,546 B1 | 12/2003 | McCord et al. | |
| 6,897,442 B2 | 5/2005 | Petrov | |
| 6,977,375 B2 | 12/2005 | Yin et al. | |
| 6,992,290 B2 * | 1/2006 | Watanabe | H01J 37/224 250/310 |
| 7,135,676 B2 | 11/2006 | Nakasuji et al. | |
| 7,462,848 B2 * | 12/2008 | Parker | B82Y 10/00 250/492.2 |
| 7,825,386 B2 | 11/2010 | Liu et al. | |
| 7,919,750 B2 * | 4/2011 | Yasuda | H01J 37/073 250/306 |
| 8,450,699 B2 * | 5/2013 | Ohshima | H01J 37/065 250/309 |
| 8,455,838 B2 | 6/2013 | Shadman et al. | |
| 8,664,594 B1 | 3/2014 | Jiang et al. | |
| 8,785,879 B1 | 7/2014 | Frosien | |
| 8,859,982 B2 * | 10/2014 | Jiang | H01J 3/029 250/396 ML |
| 8,987,692 B2 * | 3/2015 | Adamec | H01J 37/073 250/306 |
| 9,053,900 B2 * | 6/2015 | Jiang | H01J 37/05 |

(Continued)

FOREIGN PATENT DOCUMENTS

| | | |
|---|---|---|
| EP | 0150089 | 7/1985 |
| EP | 0150089 A1 | 7/1985 |

Primary Examiner — Bernard Souw
(74) Attorney, Agent, or Firm — Hodgson Russ LLP

(57) ABSTRACT

A magnetic gun lens and an electrostatic gun lens can be used in an electron beam apparatus and can help provide high resolutions for all usable electron beam currents in scanning electron microscope, review, and/or inspection uses. An extracted beam can be directed at a wafer through a beam limiting aperture using the magnetic gun lens. The electron beam also can pass through an electrostatic gun lens after the electron beam passes through the beam limiting aperture.

18 Claims, 9 Drawing Sheets

(56) References Cited

U.S. PATENT DOCUMENTS

| | | |
|---|---|---|
| 9,105,440 B2 | 8/2015 | Chen et al. |
| 9,293,293 B2 * | 3/2016 | Watanabe ............. H01J 37/065 |
| 9,437,395 B2 | 9/2016 | Li |
| 9,595,417 B2 | 3/2017 | Frosien |
| 2002/0088940 A1 | 7/2002 | Watanabe et al. |
| 2011/0186735 A1 * | 8/2011 | Fujieda ................... B01J 19/08 |
| | | 250/311 |

* cited by examiner

ELECTRON BEAM APPARATUS WITH HIGH RESOLUTIONS

FIELD OF THE DISCLOSURE

This disclosure relates to an electron beam apparatus.

BACKGROUND OF THE DISCLOSURE

Evolution of the semiconductor manufacturing industry is placing ever greater demands on yield management and, in particular, on metrology and inspection systems. Critical dimensions are shrinking while wafer size is increasing. Economics is driving the industry to decrease the time for achieving high-yield, high-value production. Thus, minimizing the total time from detecting a yield problem to fixing it determines the return-on-investment for the semiconductor manufacturer.

Micrometer and nanometer scale process control, inspection, or structuring is often done with an electron beam, which is generated and focused in an electron beam apparatus, such as electron microscopes or electron beam pattern generators. Electron or other charged particle beams offer superior spatial resolution compared to photon beams due to their short wavelengths.

Wafers can be inspected using a scanning electron microscope (SEM). FIG. 1 shows a conventional electron beam apparatus 100 in an SEM with an electron source 101, an electron beam optical column 102 (shown with dotted line), and a sample 103. The electron source 101 may be a thermal field emission (TFE) source. The sample 103 may be a semiconductor wafer. The electron beam optical column 102 commonly has multiple electrostatic and/or magnetic lenses and multiple apertures. The performance of an electron beam apparatus 100 is best characterized by the electron beam spot size at the sample (d) versus the beam current delivered to the sample because the former affects resolution and the latter affects throughput. Performance (d versus beam current or d=f(beam current)) is determined both by the electron source 101 and by the electron beam optical column 102.

To cover wide applications for SEM review and inspection, the beam current is varied from pico Amperes (pA) to hundreds of nano Amperes (nA). For each beam current, the optical spot size (d) at the sample should be minimized to reach highest resolution. For these reasons, in FIG. 1 a beam limiting aperture 104 is used to give a raw beam current (e.g., highest possible beam current to the sample 103), and a column aperture 106 is used to select the beam current from the raw beam current by changing the gun lens strength to move the first crossover 109 (XO1) position. The beam current is defined or characterized by the emission angle of the source, a, with which the source is optically related to the column. Given a selected beam current, a condenser lens 107 is used to select an optimal numeric aperture (NA) through the objective lens 108 focusing the beam to the sample 103. With an optimal NA (or the β in FIG. 1), the column lens aberrations and Coulomb interactions between electrons are balanced, and the total spot size is minimized. The electron beam profile in between the condenser lens 107 and objective lens 108 may be either with a crossover 110 (XO2) or with no crossovers.

An electrostatic gun for emitting and focusing an electron beam may consist of an electron source 101 (e.g., emission tip, suppressor, and extractor) and an electrostatic gun lens 105. The electrostatic gun lens 105 can include the ground electrodes and the focusing electrode in between the ground electrodes. A focusing voltage is applied on the focusing electrode. A beam limiting aperture 104, which may be grounded, can be included.

From an application standpoint, an electron beam apparatus can be used as an SEM platform with low beam currents below sub-nano Amperes, a review platform with medium beam currents in sub-nAs to nAs, or an inspection platform with high beam currents in nAs to hundreds of nAs. This can cover the physical defect inspection, hot spot inspection, voltage contrast inspection, or other techniques.

The disadvantage of a conventional electron beam apparatus is that the optical performance is optimized or limited in one of applications with narrow beam current ranges. For instance, an SEM review tool may provide acceptable performance with high resolutions in low beam current or medium beam current, but poor performance with high beam currents. In another example, an inspection tool is may provide acceptable performance with high beam currents, but poor performance with low beam currents or medium beam currents. FIG. 2 exhibits the simulation performance of the electron beam apparatus 100 in FIG. 1 showing how the spot size varies with the full range of beam currents. A TFE electron source 101 and an electrostatic gun lens (EGL) 105 in FIG. 1 are used in the simulation for FIG. 2. A low beam current electron beam platform like an SEM may have good performance with the electron beam apparatus 100 of FIG. 1, but a high beam current electron beam platform like inspection may have poor performance.

With different electron beam currents from pico Amperes to hundreds of nano Amperes, an electron beam apparatus may be widely used for semiconductor wafer critical dimension scanning electron microscopy, review, and/or inspection. Electron beam instrument developers have been seeking to combine all these applications into one machine with high resolution for each use. However, this is challenging because electron beam resolutions vary with electron beam currents. Therefore, an improved electron beam apparatus is needed.

BRIEF SUMMARY OF THE DISCLOSURE

In a first instance, an electron beam apparatus is provided. The electron beam apparatus comprises an electron source, a first electrostatic anode, a beam limiting aperture disposed between the electrostatic anode and the electron source, a magnetic gun lens that includes a plurality of pole pieces and coils, an electrostatic gun lens disposed on an opposite side of the beam limiting aperture from the first electrostatic anode, and a second electrostatic anode. The electron source includes a tip configured to emit electrons, a suppressor, and an extractor. The first electrostatic anode is grounded. The magnetic gun lens is disposed on either side of the electron source, first electrostatic anode, and beam limiting aperture. The second electrostatic anode is grounded and is disposed on an opposite side of the electrostatic gun lens from the first electrostatic anode. A scanning electron microscope can include this electron beam apparatus.

The electron beam apparatus can further include a chuck configured to hold a wafer, a condenser lens, an objective lens disposed between the chuck and the condenser lens, and a column aperture disposed between the second electrostatic anode and the condenser lens. The electron beam apparatus can be configured to shape the electron beam to have a first cross-over between the electrostatic gun lens and the column aperture and a second cross-over between the condenser lens and the objective lens.

The electron source may be a cold field emission source or a thermal field emission source.

In a second embodiment, a method is provided. In the method, an electron beam is generated with an electron source. The electron beam is extracted with an extractor. The electron beam is directed at a wafer through a beam limiting aperture using a magnetic gun lens that includes a plurality of pole pieces and coils and that is disposed on either side of the beam limiting aperture. The electron beam passes through an electrostatic gun lens after the electron beam passes through the beam limiting aperture.

The electron beam can be used to generate an image of the wafer.

In an instance, the magnetic guns lens is activated and the electrostatic gun lens is not activated.

The magnetic gun lens can be configured to select a beam current with a beam current switching speed.

The electron beam can pass through a column aperture, a condenser lens, and an objective lens before the electron beam reaches the wafer. The electron beam may be configured to have a first cross-over between the beam limiting aperture and the column aperture and a second cross-over between the condenser lens and the objective lens.

The electrostatic gun lens can be configured to select a beam current with a beam current switching speed.

The magnetic gun lens and the electrostatic gun lens can be configured to select a beam current with a beam current switching speed. The electron source may be a cold field emission source.

A beam current of the electron beam may be from 0.001 nA to 500 nA and a resolution of the electron beam may be from 20 nm to 80 nm. Switching beam current can occur in one second or less.

DESCRIPTION OF THE DRAWINGS

For a fuller understanding of the nature and objects of the disclosure, reference should be made to the following detailed description taken in conjunction with the accompanying drawings, in which.

DETAILED DESCRIPTION OF THE DISCLOSURE

Figure 1:
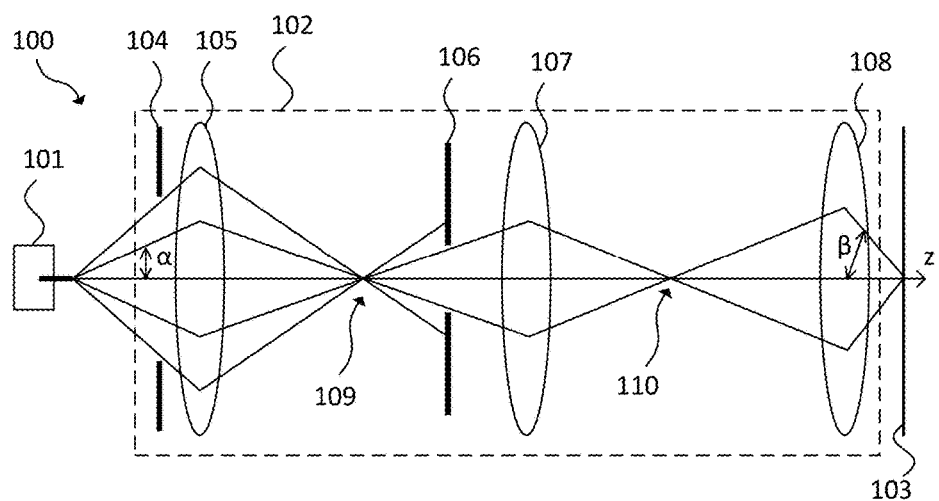
FIG. 1 is a diagram of optics in an electron beam apparatus.

Although claimed subject matter will be described in terms of certain embodiments, other embodiments, including embodiments that do not provide all of the benefits and features set forth herein, are also within the scope of this disclosure. Various structural, logical, process step, and electronic changes may be made without departing from the scope of the disclosure. Accordingly, the scope of the disclosure is defined only by reference to the appended claims.

Embodiments disclosed herein can achieve high resolutions for all usable beam currents in SEM, review, and/or inspection uses. Optical performance of the embodiments disclosed herein provide advantages over the previous designs.

The spot size (d) at the sample of an electron beam apparatus typically includes five spot size components. These are the source image $d_g$ in Equation 1, the diffraction aberration blur $d_\lambda$ in Equation 2, the chromatic aberration blur $d_c$ in Equation 3, the spherical aberration blur $d_s$ in Equation 4, and the blur of Coulomb interactions between electrons $d_{CI}$. The blur $d_{CI}$ will be described later within this disclosure.

$$d_g \propto \left(\frac{BC}{\beta^2 Br}\right)^{1/2} \qquad \text{Eq. 1}$$

$$d_\lambda \propto \frac{1}{\beta} \qquad \text{Eq. 2}$$

$$d_c \propto Cc * \Delta E * \beta \qquad \text{Eq. 3}$$

$$d_s \propto Cs * \beta^3 \qquad \text{Eq. 4}$$

In Equations 1-4, BC is beam current, β is the beam convergent angle at the sample (i.e., the numeric aperture NA), Br is the source brightness, ΔE is the source energy spread, and the Cc and Cs are the total chromatic aberration coefficient and total spherical aberration coefficient, respectively. Defined in Equations 5 and 6, the Cc and Cs include gun and objective lens chromatic and spherical aberration coefficients, respectively.

$$Cc = Cc_{OL-sp} + Cc_{gun-sp} \qquad \text{Eq. 5}$$

$$Cs = Cs_{OL-sp} + Cs_{gun-sp} \qquad \text{Eq. 6}$$

In Equations 5 and 6, $Cc_{OL\text{-}sp}$ ($Cs_{OL\text{-}sp}$) and $Cc_{gun\text{-}sp}$ ($Cs_{gun\text{-}sp}$) are chromatic (spherical) aberration coefficients of the objective lens and gun lens, respectively. These variables can be calculated at the final image (e.g., sample) side.

The performance of an electron gun is characterized by the chromatic and spherical aberration coefficients of the gun lens, i.e. $Cc_{gun\text{-}objt}$ and $Cs_{gun\text{-}objt}$, respectively. These variables can be calculated at the object side (e.g., source side) of the gun lens. Accordingly, the transformation from the gun lens aberration information ($Cc_{gun\text{-}objt}$ and $Cs_{gun\text{-}objt}$) to the final image (sample) side is related by the column optical magnification, M, in Equations 7 and 8.

$$Cc_{gun\text{-}sp} \propto M^2 * Cc_{gun\text{-}objt} \qquad \text{Eq. 7}$$

$$Cs_{gun\text{-}sp} \propto M^4 * Cs_{gun\text{-}objt} \qquad \text{Eq. 8}$$

$$M \propto \left(\frac{BC}{Ja}\right)^{1/2} \qquad \text{Eq. 9}$$

In Equations 7-9, the optical magnification, M, varies with the beam current, BC, given an electron source with a fixed angular intensity of Ja (or a fixed source brightness of Br). Note that the beam current can be selected by requirements of electron beam applications. As demonstrated using Equations 7-9, the cost of raising the beam current (or raising the machine throughput) is to magnify the gun lens aberrations to the final image (or to lose the machine resolution). This can be applied in the embodiments disclosed herein.

In a TFE based electron source, the angular intensity Ja in Equation 9 may be from approximately 0.3 to 0.6 mA/sr. The optical magnification in the column with a TFE source, such as in FIG. 1, may be divided into M<<0.05 for the SEM use with the beam currents below sub-nano Amperes, 0.01<M<0.2 for the review use with the beam currents from sub-nano Amperes to nano Amperes, and the 0.1<M<1.0 for the inspection use with the beam currents from nano Amperes to hundreds of nano Amperes.

In an electron beam optical column, the contribution of each spot size component $d_g$, $d_\lambda$, $d_c$, and $d_s$ to the total spot size, d, is fairly different in different beam currents ranges. Without including the Coulomb interactions between electrons, the total spot size d may be defined in Equation 10.

$$d = (d_g^2 + d_\lambda^2 + d_c^2 + d_s^2)^{1/2} \qquad \text{Eq. 10}$$

Figure 2:
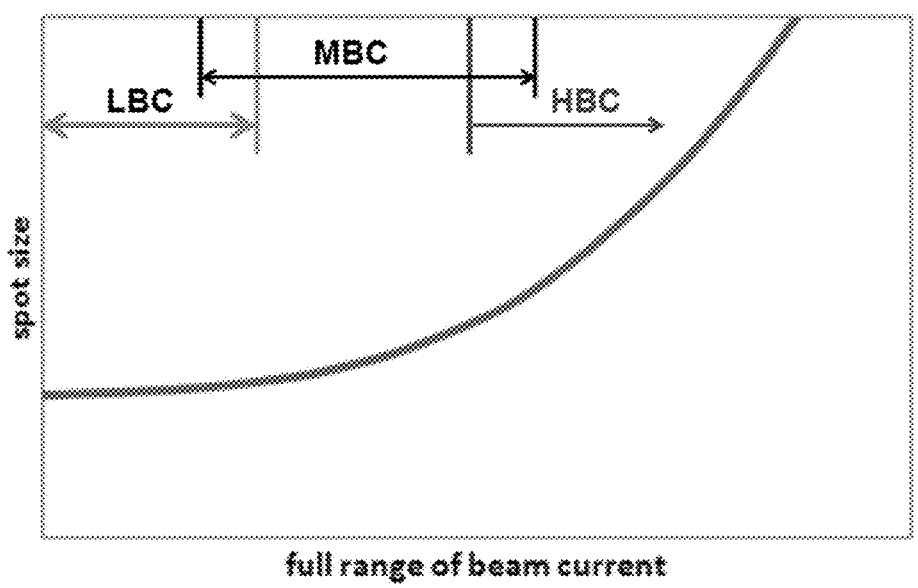
FIG. 2 is a chart of the spot size versus beam current in an electron beam apparatus with a thermal field emitter electron source and electron gun of FIG. 1.

In low beam current regime (LBC) in FIG. 2, the diffraction blur $d_\lambda$ and chromatic blur $d_c$ are dominant over others, so the minimized total spot size in low beam current regime, $d_{LB}$, is given by Equation 11.

$$d_{LB} \approx (d_\lambda^2 + d_c^2)^{1/2} \propto \Delta E^{1/2} * Cc^{1/2} \qquad \text{Eq. 11}$$

In Equation 11, $\Delta E$ is energy spread. Due to the fact that the beam current is low for SEM (below sub-nA), the optical magnification in Equation 9 may be small as well (M<<0.05). Accordingly, in Equations 5 and 7 the gun chromatic aberration contribution to the final image (sample) may be negligible, and the total chromatic aberration coefficient Cc in Equations 5 and 11 may be governed by the objective lens (i.e., $Cc \approx Cc_{OL\text{-}sp}$).

Therefore, in the low beam current regime, the spot size may be approximately independent of the beam current, gun lens aberrations, and electron source brightness.

In medium beam current regime (MBC) in FIG. 2, the source image $d_g$ and chromatic blur $d_c$ may be dominant over others, so the minimized total spot size in medium beam current regime, $d_{MB}$, may be given by Equation 12.

$$d_{MB} \approx (d_g^2 + d_c^2)^{1/2} \propto Cc^{1/2} * \left(\frac{\Delta E}{\sqrt{Br}}\right)^{1/2} * BC^{1/4} \qquad \text{Eq. 12}$$

Accordingly, the optimal spot size in the medium beam current regime can increase simultaneously with the beam current and the source ratio of energy spread to brightness ($\Delta E/\sqrt{Br}$). The total chromatic aberration coefficient Cc can include both the gun and objective lens contributions. With increasing beam current (or the optical magnification in Equation 9), the gun chromatic aberration $Cc_{gun\text{-}objt}$ may or may not be magnified sufficiently to impact and/or weigh the total Cc negligibly. It may be dependent on the gun design and the gun lens aberration $Cc_{gun\text{-}objt}$.

In high beam current regime (HBC) in FIG. 2, the source image $d_g$ and spherical blur $d_s$ may be dominant over others, so the minimized total spot size in high beam current regime, $d_{HB}$, is given by Equation 13.

$$d_{HB} \approx (d_g^2 + d_s^2)^{1/2} \propto Cs^{1/4} * \frac{1}{Br^{3/8}} * BC^{3/8} \qquad \text{Eq. 13}$$

Accordingly, the optimal spot size in the high beam current regime may increase with beam current and decreases with the brightness simultaneously. The total spherical aberration coefficient Cs may include both the gun and objective lens contributions. With increased beam current (or M in Equation 9), the gun spherical aberration $Cs_{gun\text{-}objt}$ may or may not be magnified sufficiently to impact and/or weigh the total Cs negligibly. It may be dependent on the gun design and the gun lens aberration $Cs_{gun\text{-}objt}$.

Figure 3:
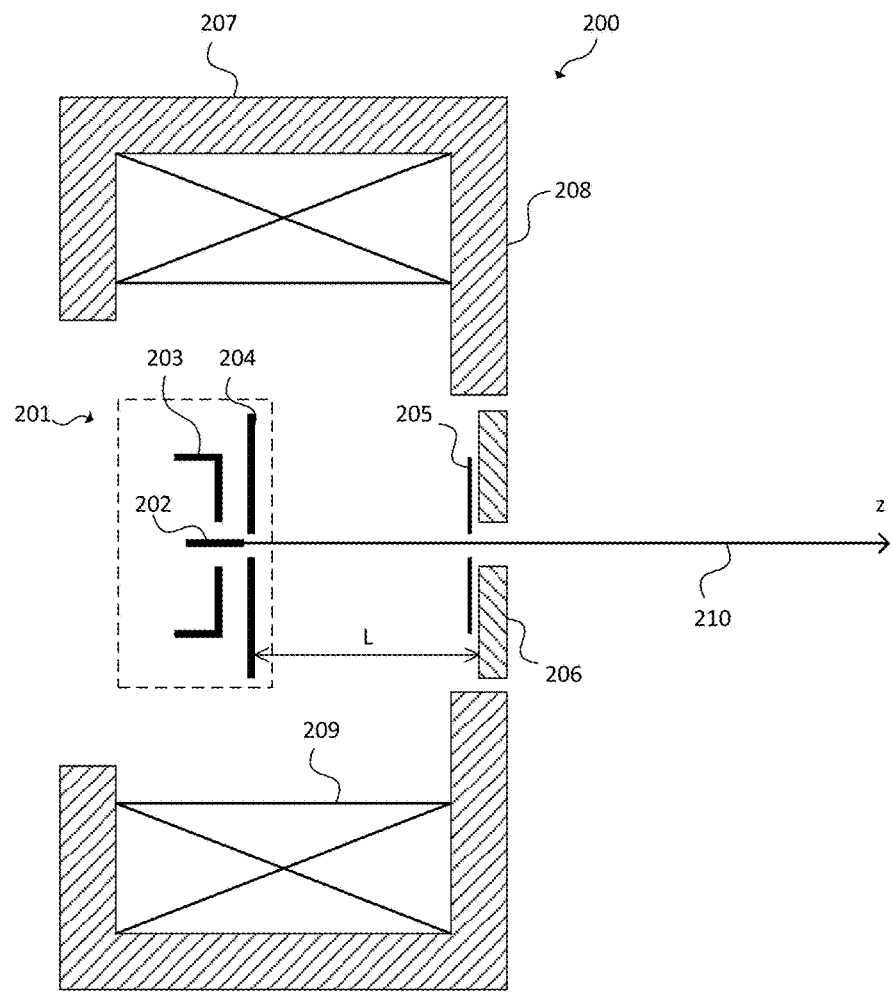
FIG. 3 is a block diagram of an embodiment of a magnetic gun with an electron source, an electrostatic anode (ground electrode), and a magnetic gun lens in accordance with the present disclosure.

As shown in FIG. 3, a magnetic gun 200 for emitting and focusing electron beam may include a magnetic gun lens (MGL) 207 and an electron source 201 (shown with dotted line) having an emission tip 202, suppressor 203, and extractor 204. A beam limiting aperture (BLA) 205 can be disposed on or proximate to the ground electrode 206 (i.e., the anode electrode) side to avoid contaminations with a too small bore. The magnetic gun lens 207 can include pole pieces 208 and coils 209. The tip 202 may be negatively biased for a given beam energy with respect to the ground electrodes 206. The suppressor 203 may be more negatively biased than the tip 202 for shaping the electron emitting beam 210. The extractor 204 may be less negatively biased than the tip 202 for pumping the electrons strongly. The gap distance L between the electron source 201 and the anode electrode of the ground electron 206 may be separated enough to avoid arcing at high beam energies.

The pole pieces 208 may be designed to narrow a magnetic flux distribution along an optical axis and form a magnetic lens in between the extractor 204 and beam limiting aperture 205, as shown later in FIG. 4. The virtual magnetic gun lens position in between the extractor 204 and beam limiting aperture 205 may be optimized to avoid magnetic saturation if the magnetic gun lens is too close to the extractor 204 and to minimize the gun lens aberration coefficients $Cc_{gun\text{-}objt}$ and $Cs_{gun\text{-}objt}$. The closer to the beam limiting aperture 205, the larger the coefficients may be. A cooling plate or cooling ring may be sandwiched in the magnetic coils 209 to avoid over-heating when the excitation Ampere-turn is up at high beam energies. The coils 209 and pole pieces 208 may be sealed in air to avoid the contamination of high vacuum. For maximizing the use efficiency of the magnetic flux in focusing the beam, the average diameter of the coil ring may be minimized to accommodate the vacuum sealing system.

Figure 4:
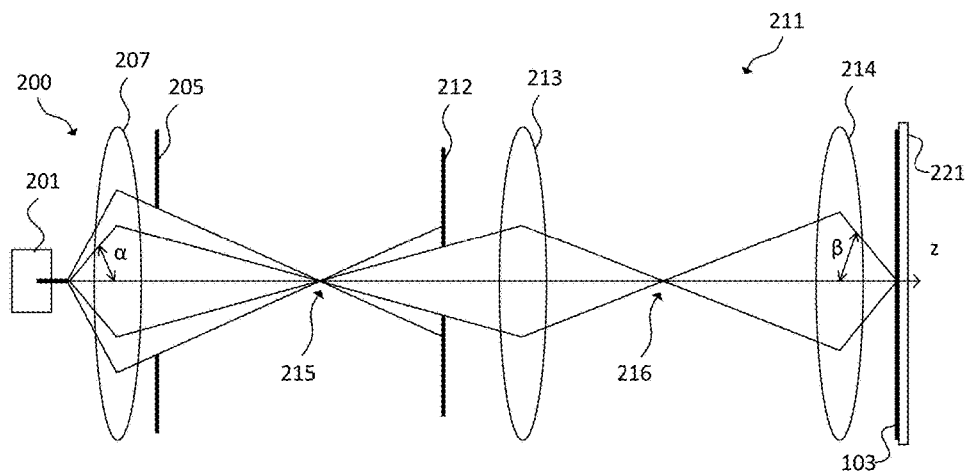
FIG. 4 is a block diagram of an embodiment of an electron beam apparatus with the magnetic gun of FIG. 3, wherein the magnetic gun lens is configured to select the beam current.

FIG. 4 shows an optical image-forming relation in an electron beam apparatus 211 with a magnetic gun 200 shown in FIG. 3, in which the magnetic gun lens 207 is used to select the beam currents. The electron beam apparatus 211 can include a sample 103, which may be a semiconductor wafer. The sample 103 may be held on a chuck 221. The electron beam apparatus 211 also can include a condenser lens 213, an objective lens 214 disposed between the chuck 221 with the sample 103 and the condenser lens 213, and a column aperture 212 disposed between electron source 201 and the condenser lens 213. The electron beam can be shaped to have a first cross-over 215 (XO1) upstream of the column aperture 212 and a second cross-over 216 (XO2) between the condenser lens 213 and the objective lens 214.

The optical performance of an electron gun can be characterized by the chromatic and spherical aberration coefficients of the gun lens (i.e., $Cc_{gun-objt}$ and $Cs_{gun-objt}$, respectively). The chromatic and spherical aberration coefficients of the gun lens can be calculated at the object side (source side) of the gun lens.

A magnetic gun performance is generally better than an electrostatic gun performance. The chromatic aberration coefficient $Cc_{gun-objt}$ and spherical aberration coefficient $Cs_{gun-objt}$ in a magnetic gun shown in FIG. 3 are approximately 10× to 30× and approximately 50× to 300× smaller than those in an electrostatic gun, respectively. These significant optical performance differences may be caused by one or more of the following two mechanisms, though other mechanisms are possible.

First, the object distance in a magnetic gun lens in FIG. 3 and FIG. 4 is shorter than that in an electrostatic gun lens in FIG. 1 because the magnetic focusing field in a magnetic lens is formed in the acceleration region between the extractor and anode in FIG. 3 and the electrostatic focusing field in an electrostatic lens is formed after the anode. Thus, the magnetic focusing field can be overlapped over the acceleration region, but the electrostatic focusing field cannot be overlapped over another electrostatic field (i.e., the acceleration field). According to electron optics theory, the longer the object distance, the larger the aberrations will be.

Second, the bore size in a magnetic gun lens is much larger than that in an electrostatic gun lens. Therefore, the electrons moving in a magnetic focusing field are relatively more paraxial than the electrons moving in an electrostatic focusing field, so the third and higher geometric aberrations in the former are much smaller than those in the latter according to electron optics theory.

Figure 5:
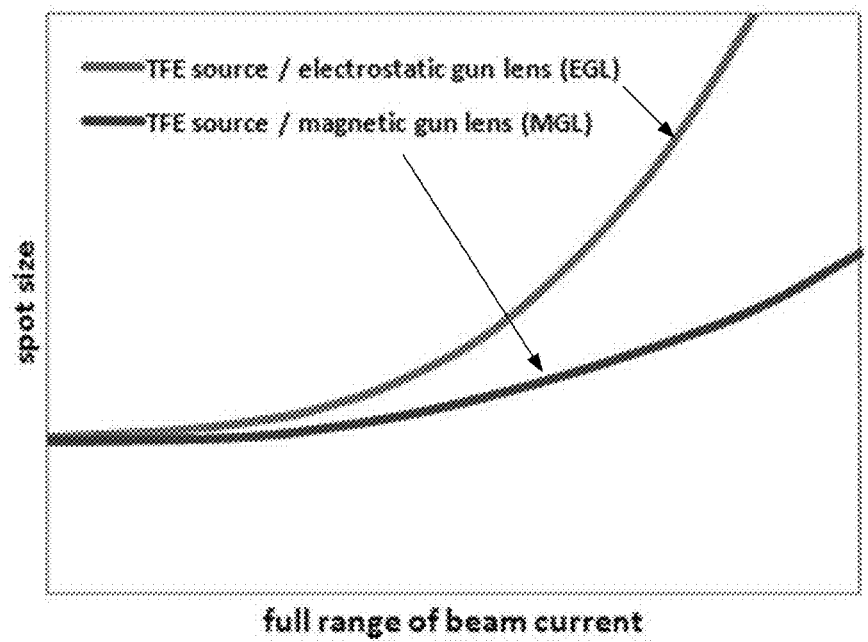
FIG. 5 is a chart of spot size versus beam current for separately using an electrostatic gun lens and a magnetic gun lens in an electron beam optical column.

FIG. 5 exhibits the spot size versus beam current comparison using an electrostatic gun lens for an electron beam optical column in FIG. 1 and a magnetic gun lens for the same column in FIG. 4. With the same TFE source, the source energy spread ΔE, brightness Br, and angular intensity Ja are all the same in FIG. 1 and FIG. 4 optical columns. A large resolution improvement with a magnetic gun lens in FIG. 4 may be due to the reduction of the gun lens aberrations, as shown in Table 1. Table 1 shows the same TFE source, but the gun lens and beam current can make the total Cc and Cs (resolution) different.

TABLE 1

|  | $Cc_{gun-objt}$ | $Cc_{gun-objt}$ | CC | | | Cs | | |
| --- | --- | --- | --- | --- | --- | --- | --- | --- |
|  |  |  | LBC | MBC | HBC | LBC | MBC | HBC |
| MGL column in FIG. 4 | 1.0 | 1.0 | $\sim Cc_{OL-sp}$ | $\sim Cc_{OL-sp}$ | $\sim Cc_{OL-sp}$ | $\sim Cs_{OL-sp}$ | $\sim Cs_{OL-sp}$ | $\sim Cs_{OL-sp}$ |
| EGL column in FIG. 1 | 10X to 30X | 50X to 300X | $\sim Cc_{OL-sp}$ | $> Cc_{OL-sp}$ | $\gg Cc_{OL-sp}$ | $\sim Cs_{OL-sp}$ | $> Cs_{OL-sp}$ | $\gg Cs_{OL-sp}$ |

In Table 1 with a magnetic gun lens (MGL) in the column in FIG. 4, the total Cc and Cs increases with the beam current negligibly. The objective lens aberrations ($Cc_{OL-sp}$ and $Cs_{OL-sp}$) may be dominant over the gun lens aberrations ($Cc_{gun-sp}$ and $Cs_{gun-sp}$) for all beam currents (or for all optical magnification M) because the gun lens aberrations ($Cc_{gun-objt}$ and $Cs_{gun-objt}$) with a magnetic lens can be greatly reduced. The optical magnification in an electron beam apparatus may be in a range of M≈0.01 to 1.0 in all applications of SEM, review, and inspections.

In Table 1 with an electrostatic gun lens (EGL) in the column in FIG. 1, if at low beam currents (LBC), a small magnification (M≪0.05) results in $Cc_{gun-sp} \ll Cc_{OL-sp}$ and $Cs_{gun-sp} \ll Cs_{OL-sp}$, such that the spot size in FIG. 5 has no significant difference between using an electrostatic gun lens (EGL) and magnetic gun lens (MGL) because the final total Cc and Cs are approximately equal to the objective lens $Cc_{OL-sp}$ and $Cs_{OL-sp}$, respectively.

In Table 1 with an electrostatic gun lens (EGL) in the column in FIG. 1, if at medium beam currents (MBC), an increasing magnification (M=0.02~0.2) results in $Cc_{gun-sp} \sim Cc_{OL-sp}$ and $Cs_{gun-sp} \sim Cs_{OL-sp}$, or the total $Cc > Cc_{OL-sp}$ and $Cs > Cs_{OL-sp}$, such that the spot size in FIG. 5 shows an increasing difference between using an electrostatic gun lens (EGL) and magnetic gun lens (MGL).

In Table 1 with an electrostatic gun lens (EGL) in the column in FIG. 1, if at high beam currents, a large magnification (M≈0.1 to 1.0) results in $Cc_{gun-sp} \gg Cc_{OL-sp}$ and $Cs_{gun-sp} \gg Cs_{OL-sp}$, or the total $Cc \gg Cc_{OL-sp}$ and $Cs \gg Cs_{OL-sp}$, such that the spot size in FIG. 5 shows a large difference between using an electrostatic gun lens (EGL) and magnetic gun lens (MGL).

Using a magnetic gun lens (MGL) in the TFE-source-based electron beam apparatus may not be able to improve resolution in low beam currents, although it improves the resolution in high beam currents, as can be seen in FIG. 5. To improve the resolution in full beam current ranges covering all uses of SEM, review, and inspections (e.g., physical defect inspection, hot spot inspection, and voltage contrast inspection), a new electron source with higher brightness can be used with the magnetic gun lens-based optical column in FIG. 4. The electron source may be a cold field emission (CFE) source.

A TFE source in FIG. 3 is a so-called Schottky emission source. The Schottky emission cathodes may be of the ZrO/W (100) type with a tip radius of approximately 0.2 to 1.0 μm. The work function can be lowered by the ZrO coating on the W, which can allow the electrons to overcome the work function at a temperature of 1800K. When the extractor voltage increases to reach an electrostatic field strength in an order of 1.0E+7 V/mm on the tip, electrons are emitted and the electron beam profile is shaped by the suppressor voltage in FIG. 3. The source brightness in Equation 1 and/or the source angular intensity in Equation 9 can be modulated by the extractor voltage.

A CFE source is based on a wave-mechanical tunneling effect. Without needing the ZrO coating on W, the electrons can be emitted from a sharp tungsten tip with a radius of approximately 0.1 μm when the tip electrostatic field strength is increased by the extractor voltage to be greater than 1.0E+8 V/mm Such high fields decrease the width of the potential wall in front of the cathode to a few nanometers so that the electrons from the Fermi level can penetrate the potential barrier by the wave-mechanical tunneling effect. Again the suppressor voltage can be used to shape the electron beam profile, and the extractor voltage can be used to modulate the brightness and/or angular intensity.

FIG. 4 shows the first embodiment, in which the electron source is a high brightness source, such as a CFE source, and the magnetic gun lens is configured in FIG. 3. Compared to the TFE source, the CFE source can have narrower source energy spread, higher brightness, and lower angular intensity, as seen in Table 2. Due to the lower Ja with a CFE source, the optical magnification can be approximately $\sqrt{5}\times$ larger at the same beam current according to Equation 9. The ratio of source energy spread to the brightness with a CFE source, $\Delta E/\sqrt{Br}$, is also $\sqrt[V]{2}/8\times$ smaller.

TABLE 2

| Source | $\Delta E$ | Br | Ja | $\Delta E/\sqrt{Br}$ | M @ same BC |
|---|---|---|---|---|---|
| TFE source | 1.0 | 1.0 | 1.0 | 1.0 | 1.0 |
| CFE source | ¼ X | 2.0 X | 0.2 X | $\sqrt{2/8}$ X | $\sqrt{5}$ X (Equation 9) |

Due to a lower angular intensity Ja with a CFE in the first embodiment, the optical magnification in the optical column in FIG. 4 can be approximately \15X larger, meaning that the magnetic gun lens aberrations $Cc_{OL\text{-}objt}$ and $Cs_{OL\text{-}objt}$ may be more magnified to the sample side, as can be summarized in Table 3.

TABLE 3

| | Cc | | | Cs | | |
|---|---|---|---|---|---|---|
| Source | LBC | MBC | HBC | LBC | MBC | HBC |
| TFE source | ~$Cc_{OL\text{-}sp}$ | ~$Cc_{OL\text{-}sp}$ | ~$Cc_{OL\text{-}sp}$ | ~$Cs_{OL\text{-}sp}$ | ~$Cs_{OL\text{-}sp}$ | ~$Cs_{OL\text{-}sp}$ |
| CFE source | ~$Cc_{OL\text{-}sp}$ | Negligibly (1.0X to 1.05X) greater than $Cc_{OL\text{-}sp}$ | Slightly (1.05X to 1.15X) greater than $Cc_{OL\text{-}sp}$ | ~$Cs_{OL\text{-}sp}$ | Slightly (1.05X to 1.15X) greater than $Cs_{OL\text{-}sp}$ | Greater (1.15X to 1.5X) than $Cs_{OL\text{-}sp}$ |

For the TFE source in a magnetic gun lens-based electron beam apparatus, the total Cc and Cs can increase with the beam current negligibly. Thus, the objective lens aberrations ($Cc_{OL\text{-}sp}$ and $Cs_{OL\text{-}sp}$) may be dominant over the gun lens aberrations ($Cc_{gun\text{-}sp}$ and $Cs_{gun\text{-}sp}$) for all beam currents (or for all optical mag M), as summarized in the Table 1.

For the CFE source in a magnetic gun lens-based electron beam apparatus, if at low beam currents (LBC), a small magnification (M<<0.05) results in $Cc_{gun\text{-}sp}$<<$Cc_{OL\text{-}sp}$ and $Cs_{gun\text{-}sp}$<<$Cs_{OL\text{-}sp}$, such that the total Cc and Cs may be approximately equal to the objective lens $Cc_{OL\text{-}sp}$ and $Cs_{OL\text{-}sp}$. Even the optical magnification in a CFE-source-based column can be approximately $\sqrt{5}\times$ larger, respectively.

For the CFE source in a magnetic gun lens-based electron beam apparatus, if at medium beam currents (MBC), an increasing magnification due both to the beam current increase and to the angular intensity decrease can result in the $Cc_{gun\text{-}sp}$ and $Cs_{gun\text{-}sp}$ larger than those in the TFE-based column. However, these are still smaller than the $Cc_{OL\text{-}sp}$ and $Cs_{OL\text{-}sp}$ because the $Cc_{gun\text{-}objt}$ and $Cs_{gun\text{-}objt}$ in a magnetic gun lens-based column are already reduced. This can lead to the total Cc and Cs slightly greater than approximately $1.05\times$ to $1.15\times$ the $Cc_{OL\text{-}sp}$ and $Cs_{OL\text{-}sp}$, respectively.

For the CFE source in a magnetic gun lens-based electron beam apparatus, if at high beam currents (HBC), a larger magnification due both to the beam current increase and to the angular intensity can decrease results in $Cc_{gun\text{-}sp}$ and $Cs_{gun\text{-}sp}$ larger than those in the TFE-based column. However, these may still be smaller than the $Cc_{OL\text{-}sp}$ and $Cs_{OL\text{-}sp}$, because the $Cc_{gun\text{-}objt}$ and $Cs_{gun\text{-}objt}$ in a magnetic gun lens-based column are already reduced. This can lead to the total Cc and Cs significantly greater than approximately $1.15\times$ to $1.5\times$ the $Cc_{OL\text{-}sp}$ and $Cs_{OL\text{-}sp}$, respectively.

Figure 6:
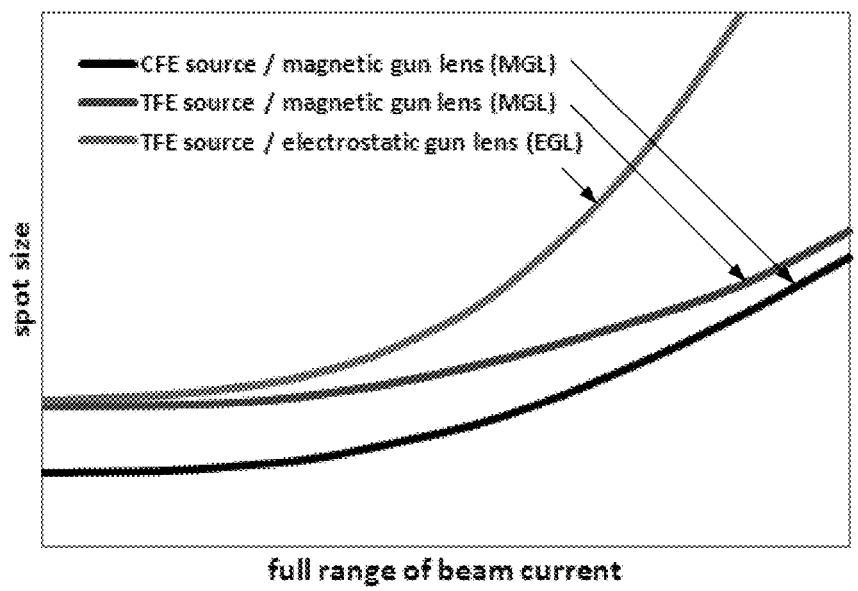
FIG. 6 is a chart of optical performance of the embodiment of the electron beam apparatus of FIG. 4 in which a cold field emission source with higher brightness is used with a magnetic gun lens.

With a CFE source and magnetic gun lens (MGL) in the first embodiment optical column in FIG. 4, the resolution in a full beam current range is improved, as can be seen in FIG. 6.

In low beam currents (LBC), the spot size given in Equation 11, $d_{LB}$, is governed by the total chromatic aberration coefficient Cc and source energy spread $\Delta E$. The $\Delta E$ with a CFE source may be approximately $0.25\times$ lower than that with a TFE source. The total Cc with a CFE source may be the same as that with a TFE source, being approximately equal to the objective lens $Cc_{OL\text{-}sp}$ in the Table 3. Accordingly, the resolution with a CFE source may be better than that with a TFE source.

In medium beam currents (MBC), the spot size given in Equation 12, $d_{MB}$, is governed by the total chromatic aberration coefficient Cc and the ratio of the source energy spread to brightness ($\Delta E/\sqrt{Br}$). According to Table 3, the Cc may only be negligibly greater than $Cc_{OL\text{-}sp}$, (almost the same as the Cc with a TFE source). However, the ratio $\Delta E/\sqrt{Br}$ with a CFE source may be approximately $\sqrt{2}/8\times$ smaller than that with a TFE source. As a combined result in Equation 12, the resolution with a CFE source may be better than that with a TFE source.

In high beam currents (HBC), the spot size given in Equation 13, $d_{HB}$, is governed by the total spherical aberration coefficient in $Cs^{1/4}$ and the source brightness in $1/Br^{3/8}$. According to Table 2 and Table 3, the Br with a CFE source may be approximately $2\times$ greater than that with a TFE source, although the Cs with a CFE source may be maximum $1.5\times$ larger than that with TFE source. However, as a combined result in Equation 13, the $Cs^{1/4}/Br^{3/8}$ with the CFE source may still be approximately 15% smaller than that with a TFE source. Accordingly, the resolution with a CFE source may be better than that with a TFE source.

Figure 7:
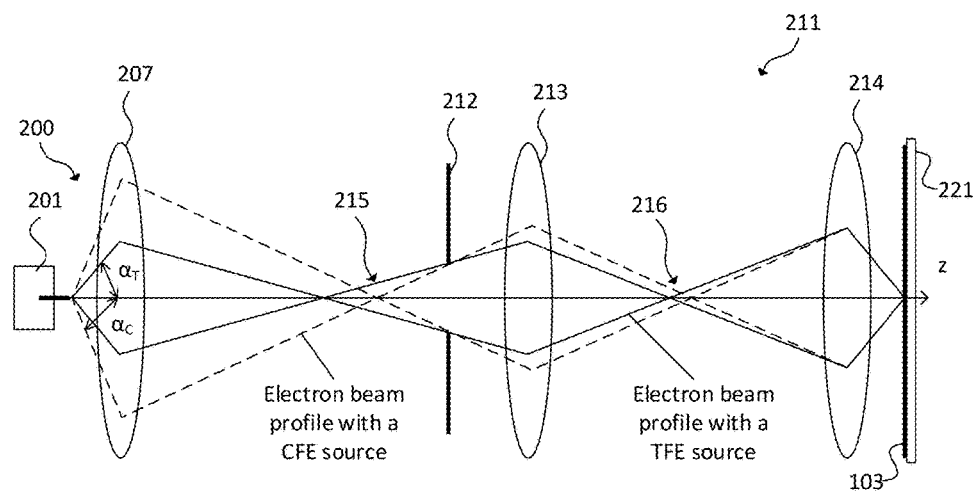
FIG. 7 is block diagram of the embodiment of the electron beam apparatus of FIG. 4 showing the reduction of influence of Coulomb interactions between electrons with a cold field emission source.

In addition to the fact that the geometric aberrations in a CFE-based column are smaller than those in a TFE-based column in FIG. 4, the blur of Coulomb interactions between electrons, do, in the former column are smaller than those in the latter column, because the electron beam volume in the former column is larger or the electron volume density is smaller than those in the latter column, as can be seen in FIG. 7. Given the same beam current, the emission angle with the CFE (ac) can be larger than that with the TFE ($\alpha_T$) because the angular intensity in former is approximately 5× lower than that in the latter (as shown in Table 2).

In the first embodiment of FIGS. 3 and 4, the optical performance with a CFE-based magnetic gun lens is improved over the TFE-based magnetic gun lens column both in current density (given the same spot size, beam current difference) and in resolution (given the same beam current, spot size difference). However, fast-switching to select and/or change the beam current can be improved.

For instance, in the defect review applications from high resolution mode to high throughput mode, or in the electron beam inspection applications from physical defect inspection to voltage contrast inspection, the beam current needs to be fast changed and/or selected differently. The magnetic gun lens in the first embodiment in FIG. 3 and FIG. 4 may be difficult to use as a fast-switcher in changing and/or selecting the beam currents.

Figure 8:
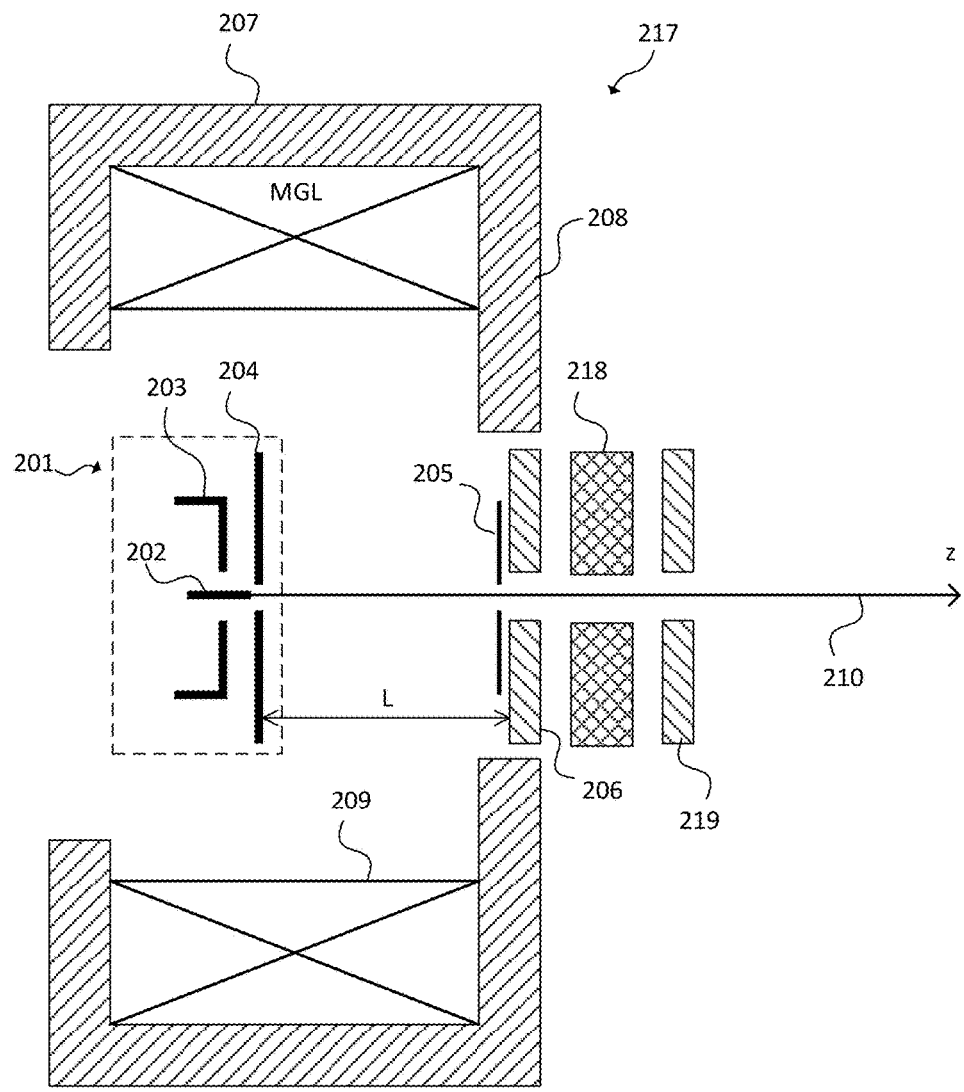
FIG. 8 is a block diagram of an embodiment of a cold field emission source-equipped mixed gun with magnetic and electrostatic lenses in accordance with the present disclosure.

FIG. 8 shows the second embodiment, in which a mixed gun 217 with magnetic and electrostatic lenses with a CFE-source is illustrated. The image-forming optics for the CFE-MGL/EGL-mixed-gun is shown in FIG. 9.

Figure 9:
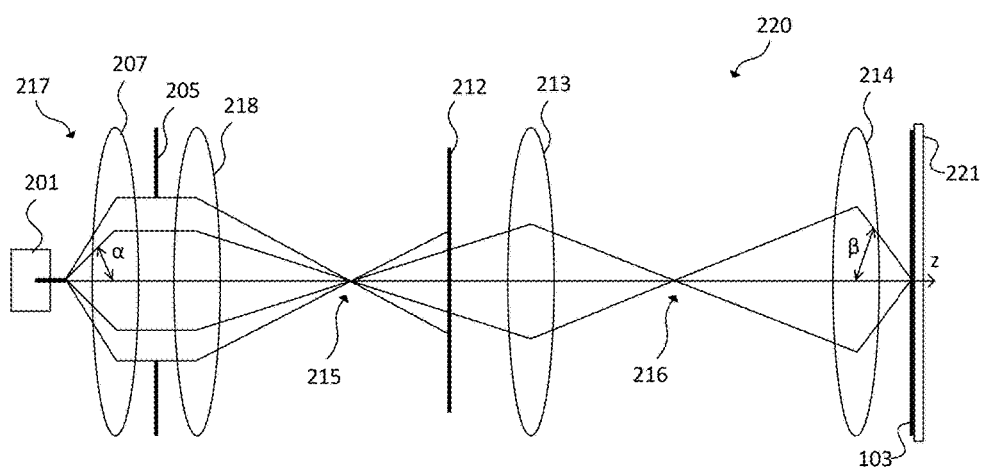
FIG. 9 is a block diagram of an embodiment of an electron beam apparatus with the cold field emission source-equipped mixed gun of FIG. 8.

In the second embodiment configuration and optics in FIG. 8 and FIG. 9, the magnetic gun lens can be first used to focus the electron beam to a telecentric-like beam and take advantage of low gun aberrations in a magnetic lens. The electrostatic gun lens can then be used to select the beam current with fast speed.

As seen in FIGS. 8 and 9, the electron beam apparatus 220 can include an electron source 201, a first electrostatic anode 206 (ground electrode), a beam limiting aperture 205, a magnetic gun lens 207, an electrostatic gun lens 218, and a second electrostatic anode 219 (ground electrode). The electron source 201 can include a tip 202 configured to emit electrons; a suppressor 203; and an extractor 204. The electron source 201 can be a cold field emission (CFE) source or a thermal field emission (TFE) source. The first electrostatic anode 206 may be grounded. The beam limiting aperture 205 can be disposed between the first electrostatic anode 206 and the electron source 201. The magnetic gun lens 207 can include a plurality of pole pieces 207 and coils 209. The magnetic gun lens 207 may have a design like that in FIG. 3. The magnetic gun lens 207 can be disposed on either side of the electron source 201, first electrostatic anode 206, and beam limiting aperture 205. The electrostatic gun lens 218 can be disposed on an opposite side of the beam limiting aperture 205 from the first electrostatic anode 206. The second electrostatic anode 219 may be is grounded and can be disposed on an opposite side of the electrostatic gun lens 218 from the first electrostatic anode 206.

The electrostatic gun lens 218 may be an Einzel lens or unipotential lens as shown in FIG. 8, or an acceleration lens or deceleration lens (two-potential lens). The electrostatic gun lens 218 can be disposed following the beam limiting aperture 205 with respect to the electron beam path, such that the beam limiting aperture 205 is sandwiched in between the magnetic gun lens 207 and electrostatic gun lens 218 to control the raw beam current. The beam limiting aperture 205 may be a part of the first electrostatic anode 206 in grounding. The beam limiting aperture 205 may be disposed sufficiently far away from the extractor 204 to allow for use of high beam energies. Except for the pole pieces 208 and coils 209, all the electrostatic components from the tip 202 to the second electrostatic anode 219 in FIG. 8 may be sealed in high vacuum.

The electron beam apparatus 220 can further include a chuck 221 configured to hold a sample 103, such as a semiconductor wafer; a condenser lens 213; an objective lens 214 disposed between the chuck 221 holding the sample 103 and the condenser lens 213; and a column aperture 212 disposed between the second electrostatic anode 219 and the condenser lens 213. The electron beam apparatus 220 can be configured to shape the electron beam to have a first crossover 215 (XO1) between the electrostatic gun lens 218 and the column aperture 212 and a second cross-over 216 (XO2) between the condenser lens 213 and the objective lens 214.

A scanning electron microscope can include an embodiment of the electron beam apparatus disclosed herein, such as that in FIGS. 8 and 9.

While illustrated as a magnetic gun lens (MGL) and electrostatic guns lens (EGL) MGL/EGL, other dual-lens mixed guns are possible. For example, an MGL/MGL, EGL/MGL, or EGL/EGL. Any these dual-lens combinations may be incorporated in the optics in FIG. 9. These other dual-lens combinations can involve replacing the MGL and EGL as illustrated in FIG. 9 with the desired pair of lenses. Each dual-lens mixed gun embodiment can be configured to provide acceptable performance for one or more applications.

Figure 10:
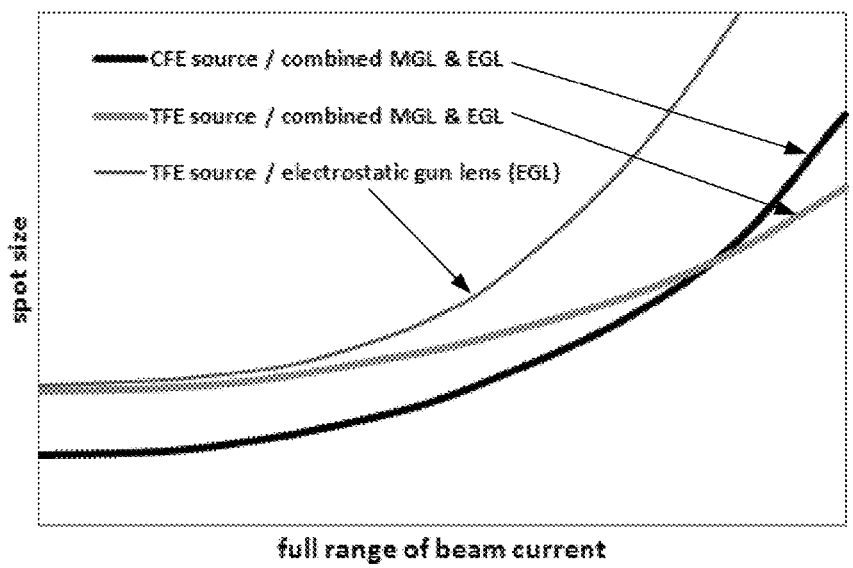
FIG. 10 is a chart showing spot size versus beam current performance and comparison of the embodiment of FIGS. 8 and 9.

FIG. 10 shows the spot size versus beam current performance and comparison in the second embodiment optics in FIG. 8 and FIG. 9. With a CFE-source in the magnetic gun lens/electrostatic gun lens mixed gun, the optical performance in a large beam current ranges (from SEM in low beam currents, review in medium beam currents to hot spot/physical defect inspections in low-end of high beam currents) is improved together with fast beam current-switching capabilities. In very high beam current regimes for voltage contrast inspection normally, the resolution may be better than the TFE-electrostatic gun lens-based optics.

Figure 11:
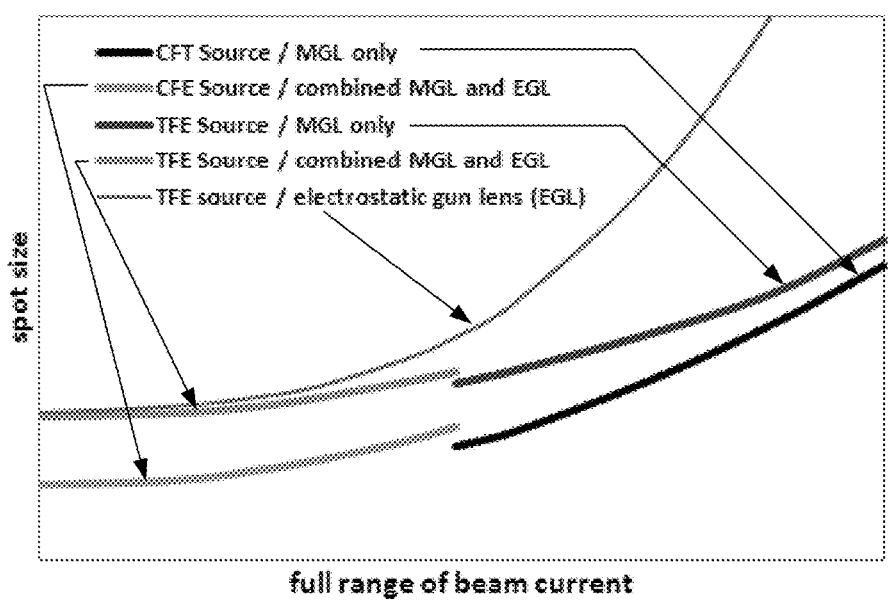
FIG. 11 is a chart showing spot size versus beam current performance and comparison of the embodiment of FIGS. 8 and 9 with mixed optical operation.

FIG. 11 shows a third embodiment. The optical operation in the third embodiment is a mixed optical operation in the first and second embodiments. The full beam current regime may be divided into a relatively low beam current range and a relatively high beam current range according to the application requirements. In the relatively low beam current range, the beam current fast-switching may be required, and in the relatively high beam current range, the beam current fast-switching may not be required. Accordingly, the magnetic gun lens/electrostatic gun lens mixed operation in the second embodiment can be used in the relatively low beam current, taking advantage of both high resolutions and beam current fast-switching. The magnetic gun lens-only operation (turning the electrostatic gun lens off) can be used in the relatively high beam currents, taking the advantage of high resolution with high beam currents.

Comparing FIG. 11 to FIG. 10, the third embodiment improves the resolutions in beam currents without losing the fast beam current-switching capabilities in a large relatively low beam current ranges.

Figure 12:
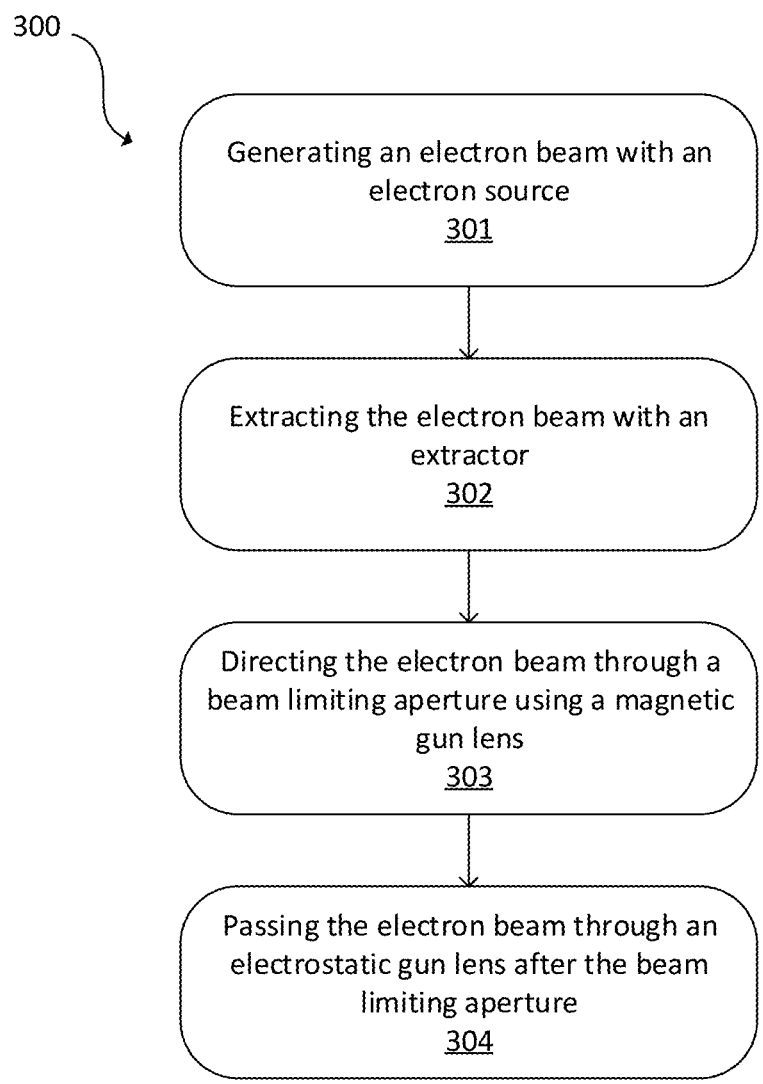
FIG. 12 is flowchart of an embodiment of a method in accordance with the present disclosure.

FIG. 12 is flowchart of an embodiment of a method 300. At 301, an electron beam is generated with an electron source. At 302, the electron beam is extracted with an extractor. The electron beam is directed at a wafer through a beam limiting aperture using a magnetic gun lens at 303. The magnetic gun lens includes a plurality of pole pieces and coils and is disposed on either side of the beam limiting aperture. At 304, the electron beam passes through an electrostatic gun lens after the electron beam passes through the beam limiting aperture. The electron beam can be used to generate an image of the wafer.

The electron beam can pass through a column aperture, a condenser lens, and an objective lens before the electron beam reaches the wafer. In an instance, the electron beam is configured to have a first cross-over between the beam limiting aperture and the column aperture and a second cross-over between the condenser lens and the objective lens.

While the magnetic gun lens and electrostatic gun lens can both be activated during operation, the electrostatic gun lens also may not be activated during operation (i.e., only the magnetic guns lens may be activated during operation).

The magnetic gun lens can be configured to select a beam current with a beam current switching speed. The electrostatic gun lens also can be configured to select a beam current with a beam current switching speed. The magnetic gun lens and the electrostatic gun lens can be configured to select a beam current with a beam current switching speed. Regardless of whether the magnetic gun lens and/or the electrostatic gun lens is configured to select a beam current with a beam current switching speed, the electron source may be a cold field emission source.

An electron beam apparatus can be used as an SEM platform with low beam currents below sub-nano Amperes (e.g., approximately 0.001 nA to 0.1 nA), a review platform with medium beam currents in sub-nAs to nAs (e.g., approximately 0.05 nA to 5 nA), and an inspection platform with high beam currents in nAs to hundreds of nAs (e.g., approximately 1 nA to 500 nA). This can cover the physical defect inspection, hot spot inspection, voltage contrast inspection, or other techniques.

A beam current of the electron beam can be from 0.001 nA to 500 nA. A spot size for SEM applications may be from 35 nm to 65 nm. Using embodiments disclosed herein, a resolution of the electron beam is from approximately 20 nm to 80 nm.

In an exemplary review application, the high resolution mode may use beam currents of from approximately 0.05 nA to 0.2 nA, and the high throughput mode may use beam currents from approximately 0.5 nA to 5 nA. In an exemplary wafer inspection application, the hot spot or physical defect inspections may use beam currents from approximately 1 nA to 20 nA, and the voltage contrast inspection may sometimes use beam currents from 50 nA to 500 nA. Beam current switching in these applications may require switching as fast as an order of second or less.

The blur induced by the Coulomb interactions between electrons may be directly related to the size of the volume of the electron beam carrying a given beam current. Assuming r(z) to be the radius of the electron beam along the optical axis z, the electron volume density, n(z), is given by Equation 14.

$$n(z) \propto \frac{BC}{r(z)^2} \quad \text{Eq. 14}$$

The average separation distance of the electrons, d(z), is given by Equation 15.

$$d(z) = n(z)^{-1/3} = \frac{r(z)^{2/3}}{BC^{1/3}} \quad \text{Eq. 15}$$

The larger the electron separation distance d(z), the weaker the Coulomb force between electrons will be because it is inversely proportional to the square of the separation d(z). As shown in FIG. 7, the electron separation distance with a CFE-based optics is larger than that with a TFE-based optics. Accordingly, the Coulomb interaction blur in CFE-based optics is reduced than compared to TFE-based optics. The reduction percentage may be varied with beam currents. The higher the beam current, the more the Coulomb effect blur may be reduced. In all the spot size versus beam current plots, the Coulomb interactions between electrons are included.

Figure 13:
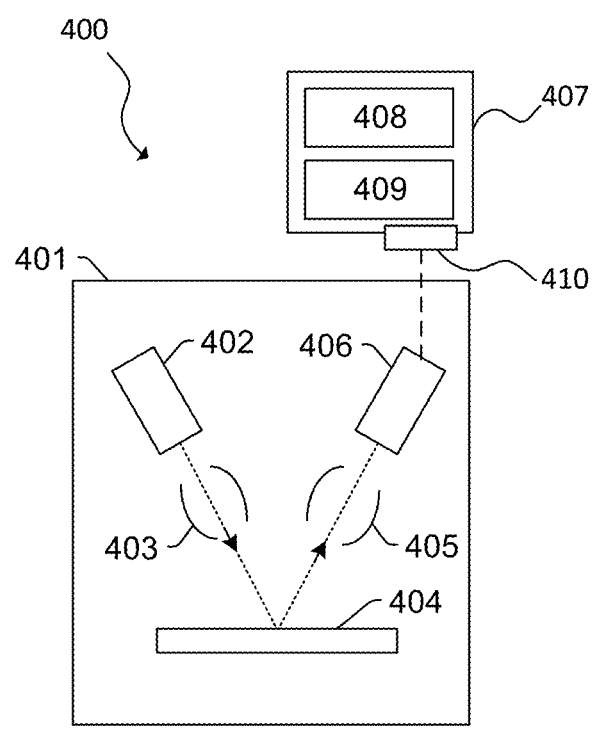
FIG. 13 is an embodiment of a scanning electron microscope system in accordance with the present disclosure.

The embodiments described herein may include or be performed in a system, such as the system 400 of FIG. 13. The system 400 includes an output acquisition subsystem that includes at least an energy source and a detector. The output acquisition subsystem may be an electron beam-based output acquisition subsystem. For example, in one embodiment, the energy directed to the wafer 404 includes electrons, and the energy detected from the wafer 404 includes electrons. In this manner, the energy source may be an electron beam source 402. In one such embodiment shown in FIG. 13, the output acquisition subsystem includes electron optical column 401, which is coupled to control unit 407. The control unit 407 can include one or more processors 408 and one or more memory 409. Each processor 408 may be in electronic communication with one or more of the memory 409. In an embodiment, the one or more processors 408 are communicatively coupled. In this regard, the one or more processors 408 may receive the image of the wafer 404 and store the image in the memory 409 of the control unit 407. The control unit 407 also may include a communication port 410 in electronic communication with at least one processor 408.

As also shown in FIG. 13, the electron optical column 401 includes electron beam source 402 configured to generate electrons that are focused to the wafer 404 by one or more elements 403. The electron beam source 402 may include an emitter and the one or more elements 403 may include, for example, a gun lens (e.g., a magnetic gun lens and/or an electrostatic gun lens), an anode, a beam limiting aperture, a gate valve, a beam current selection aperture, an objective lens, and/or a scanning subsystem. The electron column 401 may include any other suitable elements known in the art. While only one electron beam source 402 is illustrated, the system 400 may include multiple electron beam sources 402.

The electron beam source 402 and elements 403 can be or can include the components of the embodiments illustrated in FIGS. 3 and 4 or in FIGS. 8 and 9.

Electrons returned from the wafer 404 (e.g., secondary electrons) may be focused by one or more elements 405 to the detector 406. One or more elements 405 may include, for example, a scanning subsystem, which may be the same scanning subsystem included in element(s) 403. The electron column 401 may include any other suitable elements known in the art.

Although the electron column 401 is shown in FIG. 13 as being configured such that the electrons are directed to the wafer 404 at an oblique angle of incidence and are scattered from the wafer at another oblique angle, it is to be understood that the electron beam may be directed to and scattered from the wafer at any suitable angle. In addition, the electron beam-based output acquisition subsystem may be configured to use multiple modes to generate images of the wafer 404 (e.g., with different illumination angles, collection angles, etc.). The multiple modes of the electron beam-based output acquisition subsystem may be different in any image generation parameters of the output acquisition subsystem.

The control unit 407 may be in electronic communication with the detector 406 or other components of the system 400. The detector 406 may detect electrons returned from the surface of the wafer 404 thereby forming electron beam images of the wafer 404. The electron beam images may include any suitable electron beam images. The control unit 407 may be configured according to any of the embodiments described herein. The control unit 407 also may be configured to perform other functions or additional steps using the output of the detector 406 and/or the electron beam images.

It is to be appreciated that the control unit 407 may be implemented in practice by any combination of hardware, software, and firmware. Also, its functions as described herein may be performed by one unit, or divided up among different components, each of which may be implemented in turn by any combination of hardware, software, and firmware. Program code or instructions for the control unit 407 to implement various methods and functions may be stored in controller readable storage media, such as a memory 409, within the control unit 407, external to the control unit 407, or combinations thereof.

It is noted that FIG. 13 is provided herein to generally illustrate a configuration of an electron beam-based output acquisition subsystem. The electron beam-based output acquisition subsystem configuration described herein may be altered to optimize the performance of the output acquisition subsystem as is normally performed when designing a commercial output acquisition system. In addition, the system described herein or components thereof may be implemented using an existing system (e.g., by adding functionality described herein to an existing system). For some such systems, the methods described herein may be provided as optional functionality of the system (e.g., in addition to other functionality of the system).

While disclosed as part of a defect review system, the control unit 407 or methods described herein may be configured for use with inspection systems. In another embodiment, the control unit 407 or methods described herein may be configured for use with a metrology system. Thus, the embodiments as disclosed herein describe some configurations for classification that can be tailored in a number of manners for systems having different imaging capabilities that are more or less suitable for different applications.

In particular, the embodiments described herein may be installed on a computer node or computer cluster that is a component of or coupled to the detector 406 or another component of a defect review tool, a mask inspector, a virtual inspector, or other devices. In this manner, the embodiments described herein may generate output that can be used for a variety of applications that include, but are not limited to, wafer inspection, mask inspection, electron beam inspection and review, metrology, or other applications. The characteristics of the system 400 shown in FIG. 13 can be modified as described above based on the specimen for which it will generate output.

The control unit 407, other system(s), or other subsystem(s) described herein may take various forms, including a personal computer system, workstation, image computer, mainframe computer system, workstation, network appliance, internet appliance, parallel processor, or other device. In general, the term "control unit" may be broadly defined to encompass any device having one or more processors that executes instructions from a memory medium. The subsystem(s) or system(s) may also include any suitable processor known in the art, such as a parallel processor. In addition, the subsystem(s) or system(s) may include a platform with high speed processing and software, either as a standalone or a networked tool.

If the system includes more than one subsystem, then the different subsystems may be coupled to each other such that images, data, information, instructions, etc. can be sent between the subsystems. For example, one subsystem may be coupled to additional subsystem(s) by any suitable transmission media, which may include any suitable wired and/or wireless transmission media known in the art. Two or more of such subsystems may also be effectively coupled by a shared computer-readable storage medium (not shown).

In another embodiment, the control unit 407 may be communicatively coupled to any of the various components or sub-systems of system 400 in any manner known in the art. Moreover, the control unit 407 may be configured to receive and/or acquire data or information from other systems (e.g., inspection results from an inspection system such as a broad band plasma (BBP) tool, a remote database including design data and the like) by a transmission medium that may include wireline and/or wireless portions. In this manner, the transmission medium may serve as a data link between the control unit 407 and other subsystems of the system 400 or systems external to system 400.

The control unit 407 may be coupled to the components of the system 400 in any suitable manner (e.g., via one or more transmission media, which may include "wired" and/ or "wireless" transmission media) such that the control unit 407 can receive the output generated by the system 400. The control unit 407 may be configured to perform a number of functions using the output. In another example, the control unit 407 may be configured to send the output to a memory 409 or another storage medium without performing defect review on the output. The control unit 407 may be further configured as described herein.

An additional embodiment relates to a non-transitory computer-readable medium storing program instructions executable on a controller for performing a computer-implemented method. In particular, as shown in FIG. 13, the control unit 407 can include a memory 409 or other electronic data storage medium with non-transitory computer-readable medium that includes program instructions executable on the control unit 407. The computer-implemented method may include any step(s) of any method(s) described herein. The memory 409 or other electronic data storage medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes (MFC), SSE (Streaming SIMD Extension), or other technologies or methodologies, as desired.

In some embodiments, various steps, functions, and/or operations of system 400 and the methods disclosed herein are carried out by one or more of the following: electronic circuits, logic gates, multiplexers, programmable logic devices, ASICs, analog or digital controls/switches, microcontrollers, or computing systems. Program instructions implementing methods such as those described herein may be transmitted over or stored on carrier medium. The carrier medium may include a storage medium such as a read-only memory, a random access memory, a magnetic or optical disk, a non-volatile memory, a solid state memory, a magnetic tape and the like. A carrier medium may include a transmission medium such as a wire, cable, or wireless transmission link. For instance, the various steps described throughout the present disclosure may be carried out by a single control unit 407 (or computer system) or, alternatively, multiple control units 407 (or multiple computer systems). Moreover, different sub-systems of the system 400 may include one or more computing or logic systems. Therefore, the above description should not be interpreted as a limitation on the present invention but merely an illustration.

Each of the steps of the method may be performed as described herein. The methods also may include any other step(s) that can be performed by the controller and/or computer subsystem(s) or system(s) described herein. The steps can be performed by one or more computer systems, which may be configured according to any of the embodiments described herein. In addition, the methods described above may be performed by any of the system embodiments described herein.

Although the present disclosure has been described with respect to one or more particular embodiments, it will be understood that other embodiments of the present disclosure may be made without departing from the scope of the present disclosure. Hence, the present disclosure is deemed limited only by the appended claims and the reasonable interpretation thereof.

What is claimed is:

1. An electron beam apparatus comprising:
   an electron source, wherein the electron source includes:
      a tip configured to emit electrons;
      a suppressor; and
      an extractor;
   a first electrostatic anode, wherein the first electrostatic anode is grounded;
   a beam limiting aperture disposed between the electrostatic anode and the electron source;
   a magnetic gun lens that includes a plurality of pole pieces and coils, wherein the magnetic gun lens is disposed on either side of the electron source, first electrostatic anode, and beam limiting aperture;
   an electrostatic gun lens disposed on an opposite side of the beam limiting aperture from the first electrostatic anode; and
   a second electrostatic anode, wherein the second electrostatic anode is grounded and is disposed on an opposite side of the electrostatic gun lens from the first electrostatic anode.

2. The electron beam apparatus of claim 1, further comprising:
   a chuck configured to hold a wafer;
   a condenser lens;
   an objective lens disposed between the chuck and the condenser lens; and
   a column aperture disposed between the second electrostatic anode and the condenser lens.

3. The electron beam apparatus of claim 2, wherein the electron beam apparatus is configured to shape the electron beam to have a first cross-over between the electrostatic gun lens and the column aperture and a second cross-over between the condenser lens and the objective lens.

4. The electron beam source of claim 1, wherein the electron source is a cold field emission source.

5. The electron beam source of claim 1, wherein the electron source is a thermal field emission source.

6. A scanning electron microscope including the electron beam apparatus of claim 1.

7. A method comprising:
   generating an electron beam with an electron source;
   extracting the electron beam with an extractor;
   directing the electron beam at a wafer through a beam limiting aperture using a magnetic gun lens that includes a plurality of pole pieces and coils and is disposed on either side of the beam limiting aperture; and
   passing the electron beam through an electrostatic gun lens after the electron beam passes through the beam limiting aperture.

8. The method of claim 7, further comprising using the electron beam to generate an image of the wafer.

9. The method of claim 7, wherein the magnetic guns lens is activated and the electrostatic gun lens is not activated.

10. The method of claim 7, wherein the magnetic gun lens is configured to select a beam current with a beam current switching speed.

11. The method of claim 7, further comprising passing the electron beam through a column aperture, a condenser lens, and an objective lens before the electron beam reaches the wafer.

12. The method of claim 11, wherein the electron beam is configured to have a first cross-over between the beam limiting aperture and the column aperture and a second cross-over between the condenser lens and the objective lens.

13. The method of claim 7, wherein the electrostatic gun lens is configured to select a beam current with a beam current switching speed.

14. The method of claim 7, wherein the magnetic gun lens and the electrostatic gun lens are configured to select a beam current with a beam current switching speed.

15. The method of claim 14, wherein the electron source is a cold field emission source.

16. The method of claim 7, wherein a beam current of the electron beam is from 0.001 nA to 500 nA.

17. The method of claim 16, wherein a resolution of the electron beam is from 20 nm to 80 nm.

18. The method of claim 7, wherein switching beam current occurs in one second or less.

\* \* \* \* \*

UNITED STATES PATENT AND TRADEMARK OFFICE
CERTIFICATE OF CORRECTION

PATENT NO. : 10,096,447 B1  
APPLICATION NO. : 15/666666  
DATED : October 9, 2018  
INVENTOR(S) : Jiang et al.

Page 1 of 1

It is certified that error appears in the above-identified patent and that said Letters Patent is hereby corrected as shown below:

In the Claims

Column 18, Line 8, in Claim 4:
"The electron beam source of claim 1"
Should read:
--The electron beam apparatus of claim 1--;

Column 18, Line 10, in Claim 5:
"The electron beam source of claim 1"
Should read:
--The electron beam apparatus of claim 1--.

Signed and Sealed this
Twenty-second Day of September, 2020

Andrei Iancu
*Director of the United States Patent and Trademark Office*